United States Patent
Heiter

(10) Patent No.: US 12,029,673 B2
(45) Date of Patent: Jul. 9, 2024

(54) HANDCUFF

(71) Applicant: bayer Feinwerk GmbH & Co. KG, Villingen-Schwenningen (DE)

(72) Inventor: Uwe Heiter, Tuningen (DE)

(73) Assignee: BAYER FEINWERK GMBH & CO. KG, Villingen-Schwenningen (DE)

( * ) Notice: Subject to any disclaimer, the term of this patent is extended or adjusted under 35 U.S.C. 154(b) by 123 days.

(21) Appl. No.: 17/479,243

(22) Filed: Sep. 20, 2021

(65) Prior Publication Data

US 2022/0087847 A1   Mar. 24, 2022

(30) Foreign Application Priority Data

Sep. 21, 2020   (DE) .......................... 102020124538.6

(51) Int. Cl.
*A61F 5/00*   (2006.01)
*A61F 5/01*   (2006.01)

(52) U.S. Cl.
CPC .............. *A61F 5/013* (2013.01); *A61F 5/012* (2013.01)

(58) Field of Classification Search
CPC .. A61F 5/013; A61F 5/012; A61F 5/30; A61F 13/104; A61F 5/0118; A61F 2007/0035; A61F 5/05866; A61F 13/107; A61B 17/1325; A61B 18/20; A61B 90/02; A41D 13/08; A41D 13/088
See application file for complete search history.

(56) References Cited

U.S. PATENT DOCUMENTS

| | | | |
|---|---|---|---|
| 5,810,753 A | 9/1998 | Eberbach | |
| 5,865,783 A | 2/1999 | Klimoski | |
| 6,146,347 A | 11/2000 | Porrata | |
| 6,517,501 B1 * | 2/2003 | Slautterback | ......... A61F 5/0118 602/5 |

(Continued)

FOREIGN PATENT DOCUMENTS

| | | |
|---|---|---|
| DE | 102015109931 A1 | 12/2016 |
| EP | 2664306 A1 | 11/2013 |

(Continued)

OTHER PUBLICATIONS

European Search Report, EP21196159, dated Feb. 16, 2022, with translation.

(Continued)

*Primary Examiner* — Kim M Lewis
(74) *Attorney, Agent, or Firm* — Fishman Stewart PLLC

(57) ABSTRACT

A handcuff for the treatment of the carpal tunnel syndrome of a hand, the handcuff comprising a base body including a dorsal section and a palmar section. The dorsal section is adapted to exert a pressure on the dorsal side of the hand at at least one location, the palmar section is arranged to exert a pressure on the palmar side of the hand on both sides of the carpal tunnel respectively at at least one location on both sides of the carpal tunnel, and the dorsal section and the palmar section are arranged to widen the carpal tunnel of the hand by the exertion of pressure. In embodiments, the base body has, between the dorsal section and the palmar section, two substantially opposite open slots, between the dorsal section and the palmar section, and the slots are adapted to receive the thumb of the left or the right hand.

21 Claims, 11 Drawing Sheets

(56) References Cited

U.S. PATENT DOCUMENTS

| | | | |
|---|---|---|---|
| 7,182,741 B2 | 2/2007 | Porrata et al. | |
| 10,940,032 B2 | 3/2021 | Heiter | |
| 2003/0018286 A1* | 1/2003 | Porrata | A61F 5/012 |
| | | | 602/21 |
| 2004/0049141 A1* | 3/2004 | Slautterback | A61F 5/0118 |
| | | | 602/21 |
| 2005/0101898 A1* | 5/2005 | Cohen | A61F 5/0118 |
| | | | 602/21 |
| 2011/0046530 A1* | 2/2011 | Gaylord | A61F 5/0118 |
| | | | 602/21 |

FOREIGN PATENT DOCUMENTS

| | | |
|---|---|---|
| EP | 3310306 B1 | 7/2019 |
| WO | 03/007804 A2 | 1/2003 |
| WO | 03/017886 A1 | 3/2003 |

OTHER PUBLICATIONS

German Office Action, 10 2020 124 538.6, dated Sep. 21, 2020 with English Translation.
German Search Report dated Feb. 2, 2023 for German Patent Application No. 10 2020 124 538.6.
European Office Action, EP21196159.4, dated Feb. 21, 2024, with machine translation.

\* cited by examiner

HANDCUFF

CROSS-REFERENCE TO RELATED APPLICATIONS

This application claims priority to German Patent Application No. DE 10 2020 124 538.6, filed Sep. 21, 2020, the contents of which are hereby incorporated by reference in its entirety.

TECHNICAL FILED

The invention relates to a handcuff for treating a carpal tunnel syndrome of a hand.

BACKGROUND

Handcuffs are known and in use in a variety of forms and designs.

For example, WO 2003 007 804 A2 discloses a handcuff of the generic type. This handcuff can receive the left and right hand of the user, whereby the thumb is inserted in each case through a hole located laterally in the housing of the cuff.

Furthermore, a generic handcuff is known from the EP 3 310 306 B1, where the width can be adjusted to the user's hand.

The generic handcuffs, which function according to the active principle sometimes referred to as the Porrata principle (according to the inventors of WO 2003 007 804 A2), have always had a hole on the side for the thumb to stick out.

BACKGROUND

The inventors of the present invention have recognized that all known handcuffs have at least one of the following disadvantages: either the thumb must be laboriously inserted first into the cuff and then stretched ("threaded") outwardly through a hole, and/or the width of the cuff must be variable to avoid laborious "threading" of the thumb. The cuff according to the EP 3 310 306 B1 functions according to the second-mentioned principle. The second variant always results in a significantly more complicated cuff.

Among other things, the present disclosure seeks to overcome disadvantages associated with known cuffs.

SUMMARY

A handcuff according to the invention for treating carpal tunnel syndrome of a hand comprises a base body. The base body comprises a dorsal section and a palmar section, the dorsal section being adapted to exert pressure on the dorsal side of the hand at at least one location. The palmar section is adapted to exert pressure on the palmar side of the hand at at least one location on each side of the carpal tunnel. The dorsal section and the palmar section are arranged together to widen the carpal tunnel of the hand by exerting the pressure.

Between the dorsal section and the palmar section, the base body has two slots, which are essentially opposite one another and are preferably open on one side, the slots being designed to receive the thumb of the left or right hand. Furthermore, between the dorsal section and the palmar section, the base body preferably comprises two side parts adjoining the slots, which connect the dorsal section and the palmar section to one another.

These slots make it possible to eliminate the need for a hole for the thumb. The essential difference between the slots open on one side according to the present invention and the hole according to the prior art is that in known handcuffs the thumb is stretched from the inside through the hole to the outside. The thumb must therefore first be inserted into the interior of the handcuff in order to be stretched outwardly through the hole from there. This requires a correspondingly wider cuff which then fits less properly in the position of use and/or requires width adjustment. According to the present invention, thanks to the slots open on one side, it is no longer necessary to first "thread" the thumb into the interior of the handcuff.

The naming of individual sections of the handcuff and the description of their function are based on the anatomical position and direction designations of the hand. Here, "dorsal-" refers to the back of the hand or in the direction of the back of the hand. The term "palmar-" refers accordingly to the hollow or inner side of the hand. Further such pairs of terms are "distal" (in the direction of the fingertips or the fingertips or the fingertip-side end of the handcuff) and "proximal" (in the direction of the wrist or the wrist or the wrist-side end of the handcuff) as well as "thenar" (in the direction of the thumb) and "hypothenar" (in the direction of the little finger).

It should be noted here that the handcuff according to the present invention is preferably formed in an explicit manner with regard to "dorsal"/"palmar" as well as "distal"/"proximal", whereas this is not the case with regard to "thenar"/"hypothenar". In order to achieve a position of use described in more detail below, there is preferably only exactly one possibility for the user's hand to enter the handcuff with regard to "dorsal"/"palmar" as well as "distal"/"proximal". Preferably, the user's hand must be inserted at the proximal end, with the dorsal and palmar sides of the hand correctly aligned.

However, this does not apply to the thenar/hypothenar orientation of the hand. This highlights one of the advantages of the present invention: either the user's left or right hand can be inserted at the proximal end. The orientation of the hand and handcuff with regard to hypothenar/thenar does not matter.

The ability to receive both hands of the user is preferably ensured by a substantially symmetrical design of the handcuff. The corresponding symmetry plane is defined by the dorsal-palmar axis and the distal-proximal axis. Furthermore, for handcuffs having an opening in the palmar section, explained in more detail below, this symmetry plane lies substantially centrally through this opening. Furthermore, if there is a guiding ridge also explained below, it also lies in the symmetry plane. This mirror symmetrical design of the handcuff is easily understood from the figures. In the figures, the positional and directional designations are partially indicated. For the sake of clarity, however, the symmetry plane has not been drawn in.

In summary, the hand to be treated is preferably inserted into the handcuff at the proximal end, with the dorsal side of the hand in contact with the dorsal section of the handcuff. Since the handcuff does not include a predefined thenar or hypothenar section specifically designed to receive the thenar or hypothenar region of the hand, either hand of the user can be inserted into the handcuff at the proximal end.

The basic operating principle of how the carpal tunnel is widened by exerting pressure is known from the known handcuffs for the treatment of carpal tunnel syndrome and is explained in more detail in connection with the figures. This operating principle is only briefly described herein.

The palmar section exerts pressure on the palmar side of the hand. The hand cannot avoid this pressure because the dorsal section also exerts pressure on the dorsal side of the hand. The pressure exerted dorsally on the hand is usually exerted in a substantially planar or linear manner. Preferably, this means that the section exerting or applying the pressure is either planar or linear.

The palmar section applies pressure on the palmar side of the hand on both sides of the carpal tunnel. These pressures are preferably exerted linearly. On the palmar side, points of attack (or lines of attack) and effective directions of the pressures are preferably selected so that the carpal tunnel is widened. The points of attack of the pressures are preferably located on both sides next to the carpal tunnel, but not far from it. The effective directions of the pressures are preferably selected in such a way that the effective direction of the pressure, which is exerted thenar-sided on the palmar side next to the carpal tunnel, is oriented dorsal-thenar. Correspondingly, the pressure that is exerted hypothenar-sided next to the carpal tunnel on the palmar side is oriented dorsal-hypothenar. This will be explained in more detail with regard to the figures.

Said locations at which the said pressures are exerted may be punctiform, linear or planar, with planar and linear locations being preferred.

Especially preferred, pressure is exerted at exactly one point, which is preferably planar, on the dorsal side. Also especially preferred, pressure is exerted at exactly two points, which are preferably linear, on the palmar side.

The dorsal section and the palmar section can each exert the described pressure either directly or indirectly.

The pressure exerted by the palmar section (point/stretch/surface and direct or indirect) may differ from that exerted by the dorsal section.

A direct application of pressure is exerted, for example, when the dorsal section and/or the palmar section of the base body come into direct contact with the hand, which is to be treated.

An indirect application of pressure is exerted, for example, when pads are inserted between said section(s) and the hand. Furthermore, it may also be considered to place inserts distributing the pressure or generally influencing the pressure or the direction of the pressure between the base body and the hand.

The open slots for receiving the thumbs preferably run along a longitudinal axis of the handcuff, whereby the longitudinal axis corresponds to an axis running from distal to proximal. The slots are preferably open on one side at the proximal end of the handcuff, so that the hand can be inserted into the handcuff from there. In the position of use, the thumb protrudes outwardly from the interior of the handcuff through the slot. The slot preferably has an open proximal end and a closed distal end, which can serve as a stop for the thumb and thus as a limit for the insertion of the hand.

Both the right hand and the left hand can be inserted into the proximal end of the handcuff through the slots, which are arranged opposite each other. The slots are preferably recesses open on one side and elongated in shape, with the open ends of the slots preferably located at the proximal end of the handcuff.

After the hand has been fully inserted into the handcuff, the handcuff and the hand can be referred to as being in a position of use.

The base body preferably forms the framework of the handcuff. However, the handcuff can also consist exclusively of the base body. Apart from the base body, the handcuff may further comprise pads, inserts, inflatable and/or position-variable elements such as pressure build-up elements or the like, some of which have already been mentioned above. Pads and inserts may serve to provide comfort and/or pressure build-up and/or an alignment of the pressure or its effective direction. Pressure build-up elements are preferably air cushions or special screws that build up pressure on the desired section of the hand when screwed in. Preferably, the handcuff comprises exactly one pressure build-up element.

The handcuff can be connected to a compressor or a pump ball, for example, to inflate the pressure build-up elements. Pump balls, in particular those with manometer and valve, are robust and well suited for use with the handcuff according to the invention. Pump balls with manometer and valve are known from known manually operated blood pressure measuring devices. By actuating the pump ball, the pressure build-up element is inflated, whereby the pressure is controlled with the manometer. The manually operated valve is used to manually release the air. Such pump balls are preferably permanently connected to the handcuff via a hose.

However, other devices for pumping air can also be used to inflate the pressure build-up elements. In general, the handcuff preferably includes such a device and a manometer for indicating the pressure in the pressure build-up element. The aforementioned device and manometer can also be placed directly on the main body of the handcuff, so that the hose can be dispensed with. This is advantageous if users take the handcuff with them on trips, for example, and the two-part arrangement of pump ball with manometer on the one hand and base body on the other, which is connected via the hose, is impractical.

Devices for pumping air can also be used, which are known from known fully automatic blood pressure measuring devices, in which the pumping up does not take place manually. Usually, these are compressors.

All embodiments of the present invention include the slots described above for receiving the thumbs of the right and left hand. This has the advantage that both hands can be inserted effortlessly into the handcuff at the proximal end. This requires no unfolding, widening or the like of the handcuff and also no "threading" of the hand and in particular the thumb. Most cuffs of the prior art include a hole through which the thumb of the hand received inside the cuff is extended outwardly. This complicates the construction and handling of known handcuffs. The slots open on one side for receiving the thumb according to the cuff of the invention overcome these disadvantages.

It should also be mentioned that even the very simple embodiment of the present invention described above, which does not require the air cushions etc. described below and consists essentially or even exclusively of the base body, can already reliably achieve the desired widening of the carpal tunnel. The pressure required for this, which has already been described in detail above, can be generated in several ways.

On the one hand, the handcuff may be made essentially of a rigid material. In this example, the pressure is generated simply by inserting the hand into the handcuff, if the distance between the palmar section and the dorsal section is somewhat smaller than the distance between the palmar and dorsal sides of the hand to be treated. This causes the hand to be slightly squeezed during the insertion, which results in the desired pressure.

On the other hand, the handcuff can be made at least partially of a flexible, i.e. yielding or elastic, material. In this case, too, the distance between the palmar section and the dorsal section is selected to be somewhat smaller than the distance between the palmar and dorsal sides of the hand to be treated. During the insertion, however, the distance between the dorsal and palmar sections of the handcuff is increased by the flexibility of the material. This creates a restoring force, which is transmitted from the dorsal and palmar sections of the handcuff to the dorsal and palmar sides of the hand.

Another advantage of all handcuffs according to the invention compared to the prior art is that their design can receive large, medium and small hands without adjustment of the base body or other manipulations. Small hands are simply inserted further into the handcuff than large hands. With large hands, the problem in the prior art was often that the width of the handcuff required adjustment. In this regard, the slots of the handcuff according to the invention are again advantageous, since the thumb is extended outwards through one slot and the opposite slot allows the hypothenar region of the hand to be partially extended in the case of very large hands. In other words, with very wide hands, both the thumb and the region of the hand opposite the thumb can extend outward a little from inside the handcuff through the slots.

A distance between the dorsal section and the palmar section may increase from a distal end to a proximal end of the base body.

The base body can thus taper toward the distal end. This tapering corresponds to the anatomy of the hand, whose dorsal-palmar extension (its height, so to speak) is significantly greater near the wrist than near the fingertips. This distance between the dorsal and palmar sections can be measured perpendicular to an imaginary mid-longitudinal axis of the handcuff, this imaginary mid-longitudinal axis being the proximal-distal axis.

If the distance between the dorsal and palmar sections decreases towards the distal end, the hand is already advantageously pressurized by the aforementioned sections during the insertion. The reason is that the hand is thicker or, as it were, "higher" toward the wrist (i.e., at its proximal end) than near the fingertips. The further these thicker or higher sections of the hand are pushed into the cuff, the greater the pressure exerted on them by the cuff.

It is well known that the exertion of pressure for the purpose of widening the carpal tunnel is achieved with generic handcuffs close to the ball of the hand, i.e. at the proximal end of the hand. For this reason, the protruding variant with the distance between the dorsal and palmar sections tapering towards the distal end of the cuff is advantageous.

It may additionally or alternatively be considered to increase a width of the base body from the distal end to the proximal end. This widening may affect the entire base body or only a distal section of the base body. The width is measured in thenar-hypothenar direction that is orthogonal to the distal-proximal axis and to the dorsal-palmar axis. This also corresponds to the anatomy of the hand, whose width decreases towards the fingertips.

The handcuff may include at least one guiding ridge in a distal section of the base body, wherein the at least one guiding ridge may be arranged to lie between two fingers of the hand in a position of use, thereby providing effective orientation of the hand for treatment. The at least one guiding ridge thus causes the hand, and in particular the carpal tunnel thereof, to be correctly positioned within the handcuff.

It may be thought of exactly one guiding ridge, which, in the position of use, lies between the middle finger and the ring finger of the hand to be treated. Of course, it can also be considered that the guiding ridge is located between the middle finger and the index finger or between the little finger and the ring finger. It may also be thought of providing two or all three of the guiding ridges arranged as described above.

The extent of the at least one guiding ridge in the longitudinal direction, i.e. along the distal-proximal axis, is preferably dimensioned so that it is shorter than the space between the fingers in question. Preferably, the above-described slot of the base body already serves as a stop for the thumb and already sufficiently limits the insertion of the hand into the handcuff However, it may also be considered that the at least one guiding ridge is used as an additional stop and thus as a limitation for the insertion of the hand into the handcuff.

It may also be considered that the at least one guiding ridge is variable in length along the distal-proximal axis. The at least one guiding ridge can, for example, be designed to be retractable or compressible. This can additionally improve the safe positioning of hands of different sizes. Such a design can be advantageous in some versions/embodiments, but is not absolutely necessary.

The base body may be substantially similar in profile to a flattened circle, a flattened oval or a flattened C.

The base body can be designed to be resilient in such a way that the distance between the dorsal section and the palmar section increases when the hand is inserted, thereby providing the pressure to widen the carpal tunnel in the position of use. The dorsal section and/or the palmar section thus act as springs, which are pretensioned by the hand itself during the insertion. The restoring force of this at least one resilient section then provides the pressure to widen the carpal tunnel. In this case, separate pressure build-up elements can be dispensed with.

Alternatively, as explained above, the base body can be rigid so that neither the dorsal section nor the palmar section act resiliently. In this case, pressure can be provided by pushing the hand into the handcuff under appropriate pressure. Once the hand has reached the position of use, the necessary pressure is provided, for example, by shaping the palmar and dorsal sections and compressing the hand during the insertion. In this case, too, there is no need for a separate pressure build-up element.

Of course, the aforementioned embodiments can also be equipped with pressure build-up elements. These can be used as an alternative or in addition to the pressure build-up options described above.

The springy design of the base body described above thus provides a particularly simple and efficient pressure build-up, with no further aids such as air cushions being required. However, it is of course possible to use the resilient design in combination with an air cushion or the like described in more detail below.

The palmar section may comprise a first and a second hypo/thenar section, and the distance between the two hypo/thenar sections may change. Depending on whether the left or right hand is inserted into the handcuff, one of the two hypo/thenar sections functions as the thenar section and the opposite section as the hypothenar section. The hypo/thenar section that receives the user's thumb functions as the thenar section. The opposite hypo/thenar section functions accordingly as a hypothenar section.

The hypo/thenar section acting as the thenar section is located on the thumb side laterally of the carpal tunnel, so to speak. The hypo/thenar section acting as the hypothenar section lies on the opposite side laterally of the carpal tunnel.

It should be noted here that both hypo/thenar sections exert (preferably linear) pressure on the hand, preferably on both sides immediately adjacent to the carpal tunnel. The designations "thenar" and "hypothenar" only indicate on which side of the carpal tunnel the section in question is located that exerts the pressure. Both are nevertheless essentially in the middle and are in contact with the palmar section of the hand in the position of use.

The effective directions of the pressure exerted by the hypothenar section on the corresponding area of the palmar side run both dorsally and hypothenarly, so to speak obliquely towards the outer edge of the hand on which the little finger is located. Correspondingly, the effective direction of the pressure exerted by the thenar section on the corresponding area of the palmar side runs obliquely, so to speak, towards the opposite outer edge of the hand, i.e. dorsal-thenar.

The fact that the distance between the two hypo/thenar sections can increase when the hand is inserted results in a very efficient exertion of pressure to widen the carpal tunnel. In particular, the possibility of increasing the distance ensures that the pressure is exerted with optimal direction of action on the palmar region of the hand on both sides of the carpal tunnel.

The possibility of increasing the distance between the hypo/thenar sections can be provided in several ways. On the one hand, an opening running longitudinally, i.e. along the distal-proximal axis, can be thought of between the first and second hypo/thenar sections. This opening may be slot-shaped. It is described in more detail below. On the other hand, a flexible region may also be thought of which connects the first and second hypo/thenar sections and allows the distance between the two sections to be increased. Alternatively, for example, a groove could be thought of, whose opening points into the interior of the handcuff and which can allow the aforementioned change of the distance.

Preferably, the build-up of pressure on the hand, which is caused either by the insertion of the hand or by corresponding pressure build-up elements such as air cushions, leads to an increase in the distance between the first and second hypo/thenar sections. This usually requires a certain flexibility of the aforementioned sections. The increase in the distance between the hypo/thenar sections, while these are already in close contact with the palmar side of the hand on both sides of the carpal tunnel, in conjunction with the restoring force caused by the increase in the distance between the dorsal and palmar sections, ultimately effect the pressure which widens the carpal tunnel as desired.

In embodiments without the variable distance between the hypo/thenar sections described above, the palmar section preferably comprises superstructures or specially shaped sections which, with regard to the effective direction and point of attack of the forces or pressures, ensure that the widening of the carpal tunnel takes place even without increasing the distance between the hypo/thenar sections and that the desired effective direction of the pressure on the palmar side of the hand is achieved.

Increasing the distance between the hypo/thenar sections can already produce the desired effect if it is in the range of a few millimeters or even a few tenths of a millimeter. The range of a few millimeters is preferred here.

The handcuff can have an opening between the hypo/thenar sections. This opening can be, for example, in the form of the slot described above. Alternative designs of the opening are conceivable.

The opening may be continuous so that the handcuff is substantially C-shaped in profile. The opening extends along the distal-proximal axis along the entire length of the handcuff.

If the opening is not continuous, only a section that accommodates the non-continuous opening may be substantially C-shape in profile. This is the case, for example, if the opening is only present in a proximal section of the handcuff, and there ensures the function of the hypo/thenar sections described above. If at the same time there is no opening in the distal section, this also ensures high stability of the handcuff. Through the length of the slot-shaped opening it can be determined, for example, how far apart the hypo/thenar sections can move and/or what force must be overcome for this. Indirectly, the length of the aforementioned opening can thus be used to control the application of force into the hand.

Alternatively, the selection of a material from which the handcuff is made can determine how far apart the hypo/thenar sections can move and/or what force must be overcome for this. In particular, an elasticity of the material is important here, since a desired restoring force can be generated by bending elastic hypo/thenar sections. Furthermore, the structure of the handcuff, for example a thickness of the base body and/or reinforcing ribs attached to the base body, can also perform this function.

An additional advantage of the opening is that it allows easy visual inspection by the user. Since the two hypo/thenar sections are positioned on either side of the carpal tunnel, the opening is immediate above the carpal tunnel in the position of use (when the palmar region of the hand is viewed). The user can therefore position the handcuff correctly by simply ensuring that the opening is above the carpal tunnel. Based on the characteristic course of the externally visible tendons, muscles and lines on the palmar side of the hand, the user can easily determine for himself where the carpal tunnel is located on his hand and thus also perform the aforementioned correct positioning easily himself.

The handcuff can comprise a pressure build-up element at the dorsal section, wherein the pressure build-up element is arranged to exert pressure on the dorsal side of the hand at at least one point. The pressure build-up element maybe, for example, a screw, an air cushion or the like. Such pressure build-up elements are known from the prior art and are already used in known handcuffs.

The base body of the handcuff can be designed as a single piece. This simplifies both manufacture and use.

The base body is preferably made of a plastic or other elastic material.

BRIEF DESCRIPTION OF THE DRAWINGS

Further advantages, features and details of the invention result from the following description of preferred embodiment and from the drawing; these show in.

For clarity, not all reference numbers are shown in all figures.

DETAILED DESCRIPTION

Figure 1:
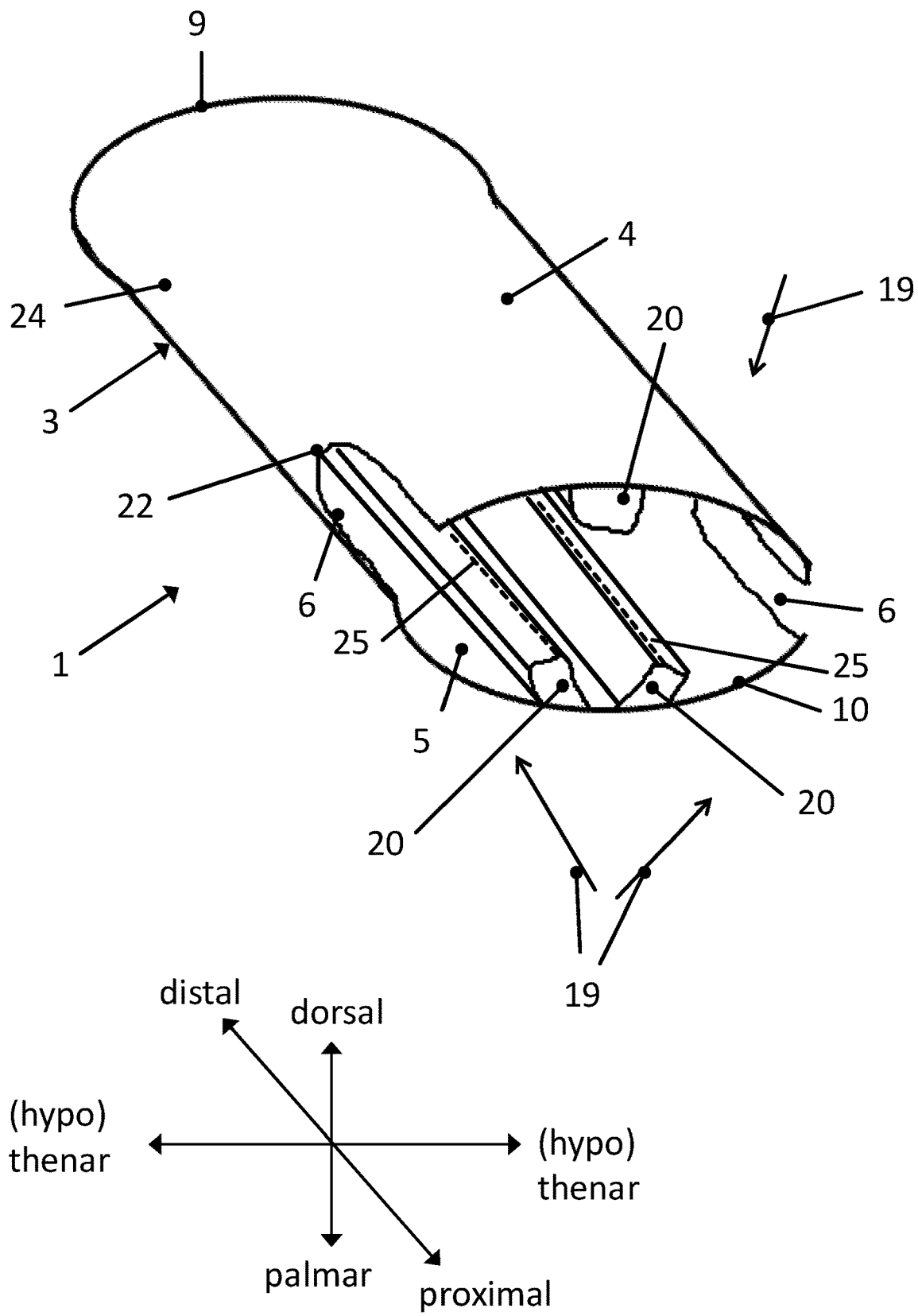
FIG. 1 is a schematic view of a first embodiment of a handcuff according to the present invention.

FIG. 1 shows a handcuff 1. In FIG. 1, a base body 3 with a dorsal section 4 and a palmar section 5 as well as slots 6 and side parts 24 located there between can be seen. Furthermore, a distal end 9 and a proximal end 10 are indicated. In the interior of the base body 3, specially shaped sections 20 can be seen, whose function will be explained in more detail below.

Furthermore, a distal slot end 22 can be seen, which can serve as a stop for a thumb 7 (not shown) or at least limits an insertion depth of the hand 2 to be treated.

Furthermore, a coordinate system is drawn next to FIG. 1 to illustrate the directions and axes (distal, proximal, dorsal, palmar, and (hypo)-thenar with regard to the handcuff 1 shown in FIG. 1.

Figure 2:
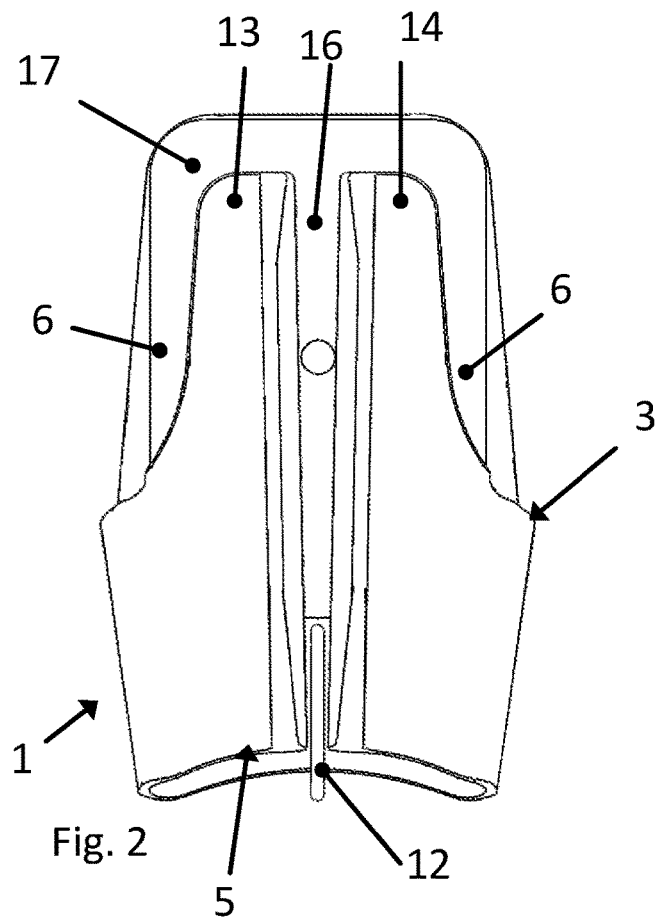
FIGS. 2 to 12B illustrate various views of a second embodiment of a handcuff according to the present invention.

FIG. 2 shows a view from below of a second embodiment of a handcuff 1. A palmar section 5 comprising a first hypo/thenar section 13 and a second hypo/thenar section 14 can also be seen. Furthermore, a pressure build-up element 17 in the form of an air cushion and a guiding ridge 12 can be seen. Laterally, the slots 6 are recognizable. Furthermore, a distal-proximal opening 16 is visible between the two hypo/thenar sections 13, 14.

Figure 3:
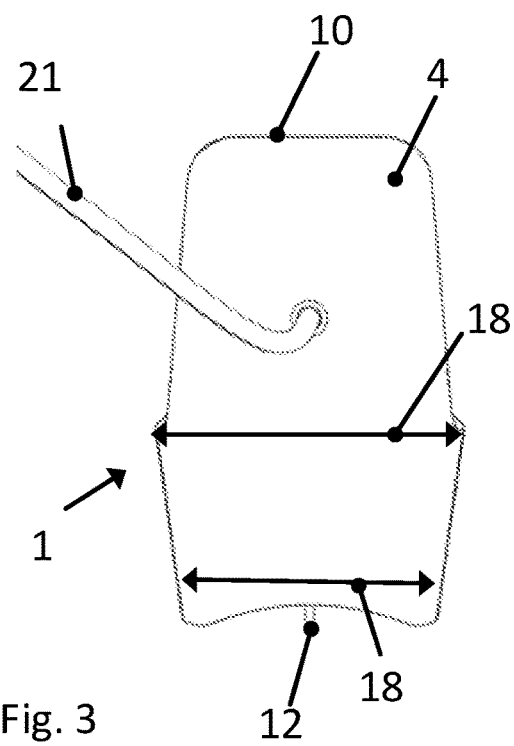

FIG. 3 shows a view of the dorsal section 4 of the handcuff 1 from FIG. 2. Furthermore, a width 18 of the handcuff 1 is drawn at two places. Furthermore, a part of a hose 21, which supplies the air cushion 17, can be seen. FIG. 3 shows, that only the width 18 of the distal section 11 (cf. FIGS. 7 and 12.1), which completely encloses the user's hand 2 also by means of side parts 24 to be described, increases towards the proximal end 10. The proximal section 23 of the base body 3, which laterally encloses the slots 6, does not widen towards the proximal end 10.

Figure 4:
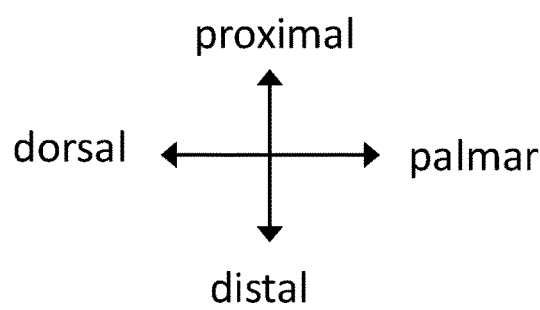
Figure 4:
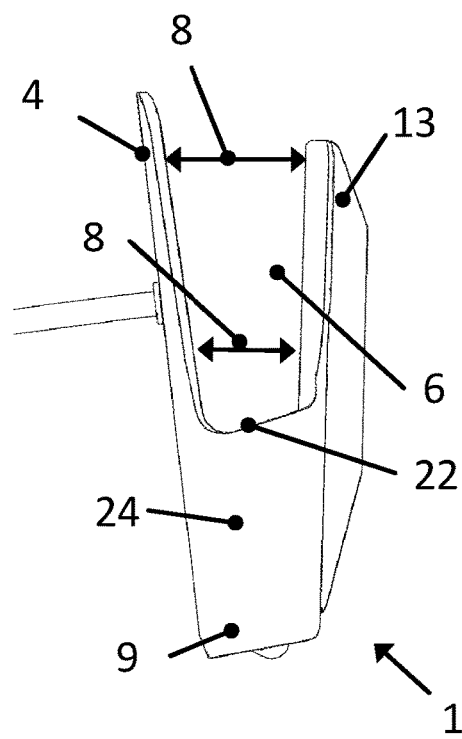

FIG. 4 shows a side view of the handcuff 1 from FIG. 2. Furthermore, the directions or axes (proximal and distal as well as dorsal and palmar) are indicated with reference to FIG. 4. Furthermore, a distance 8 between dorsal and palmar sections 4, 5 is drawn at two places.

Figure 5:
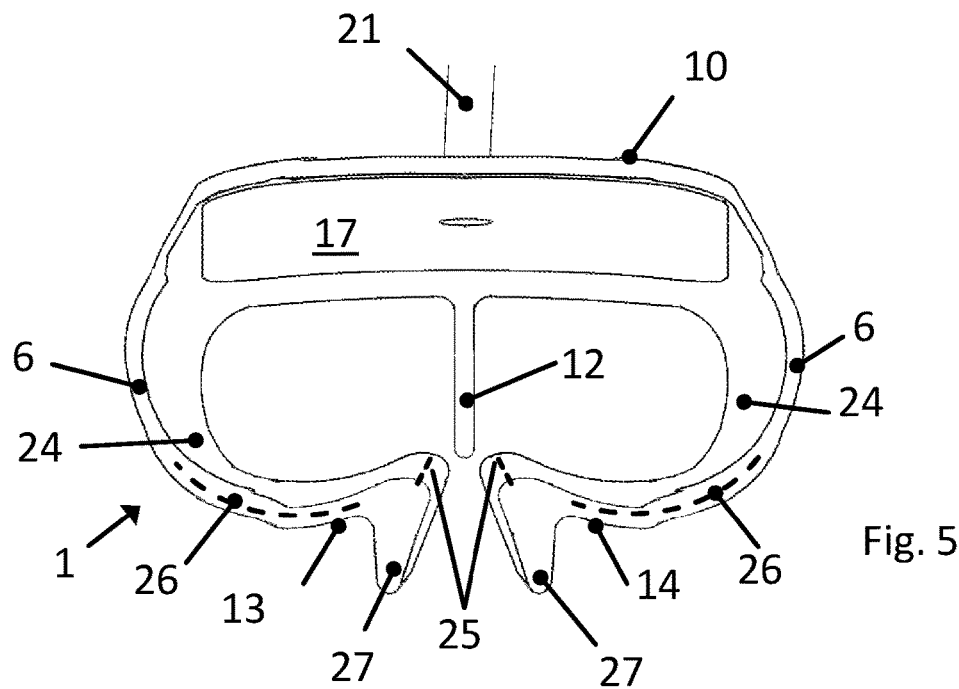

FIG. 5 shows a view of the proximal end 10 of the handcuff 1 of FIG. 2.

Figure 6:
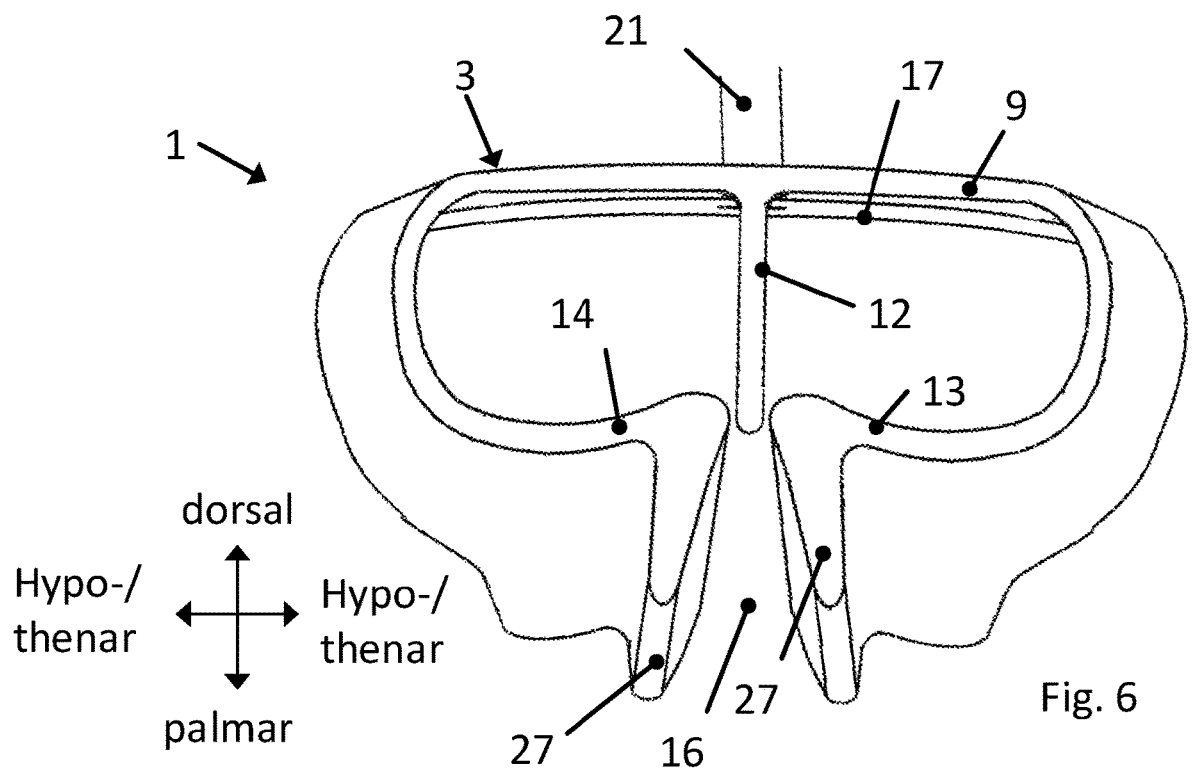

FIG. 6 shows a view of the distal end 9 of the handcuff 1 of FIG. 2. With reference to FIG. 6, the dorsal and palmar directions or axes are indicated, as well as the two hypo-/thenar directions or axes.

Figure 7:
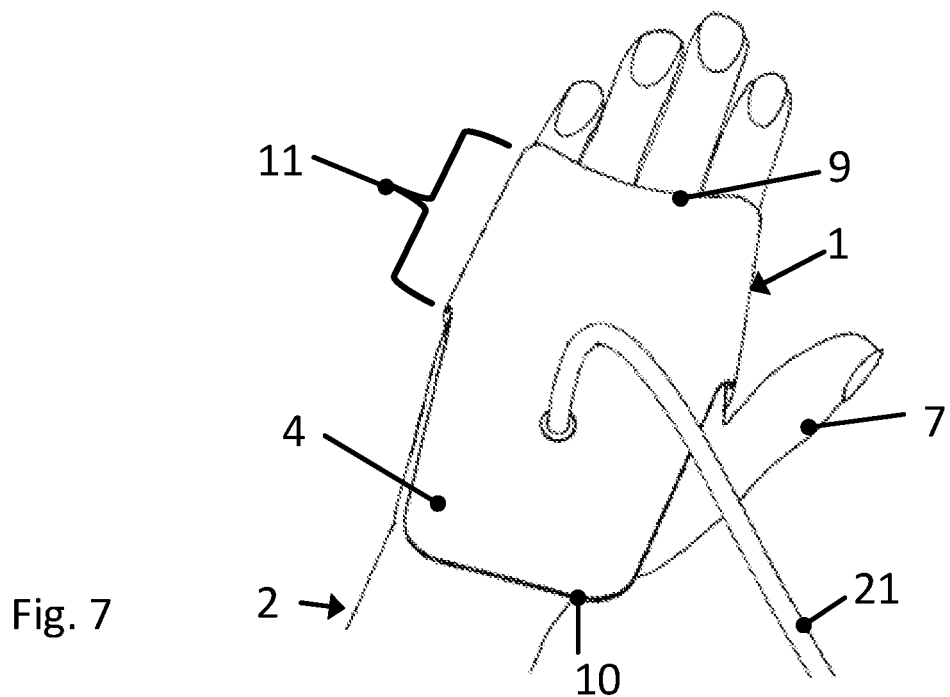

In FIG. 7, a view of the dorsal section 4 of the handcuff 1 of FIG. 2 is shown, in which the left hand 2 of a user is located. The thumb 7 of the hand 2 can be seen. Furthermore, a distal section 11 of the handcuff 1 is also indicated.

Figure 8:
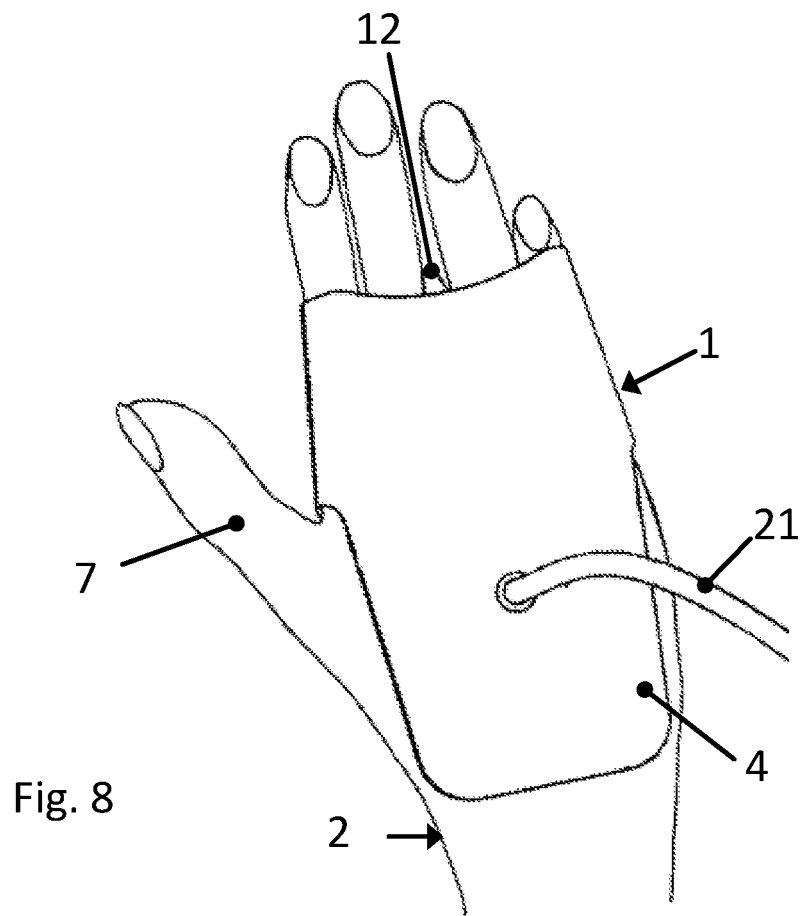

In FIG. 8, a view of the dorsal section 4 of the handcuff 1 of FIG. 2 is shown, in which the right hand 2 of a user is located.

Figure 9:
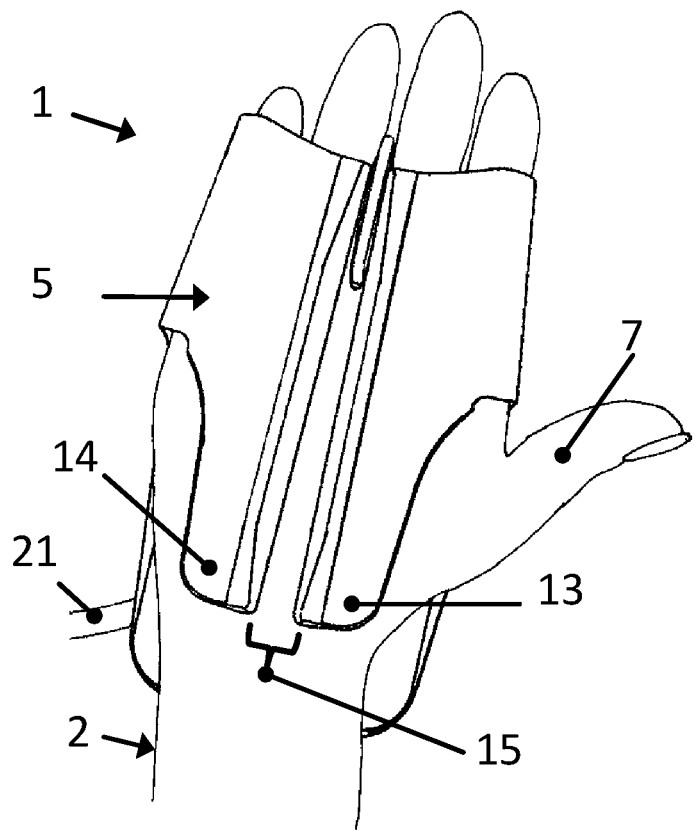

In FIG. 9, a view of the palmar section 5 of the handcuff 1 from FIG. 2 is shown, in which the right hand 2 of a user is located. Furthermore, a distance 15 between the two hypo/thenar sections 13, 14 is drawn in FIG. 9.

Figure 10:
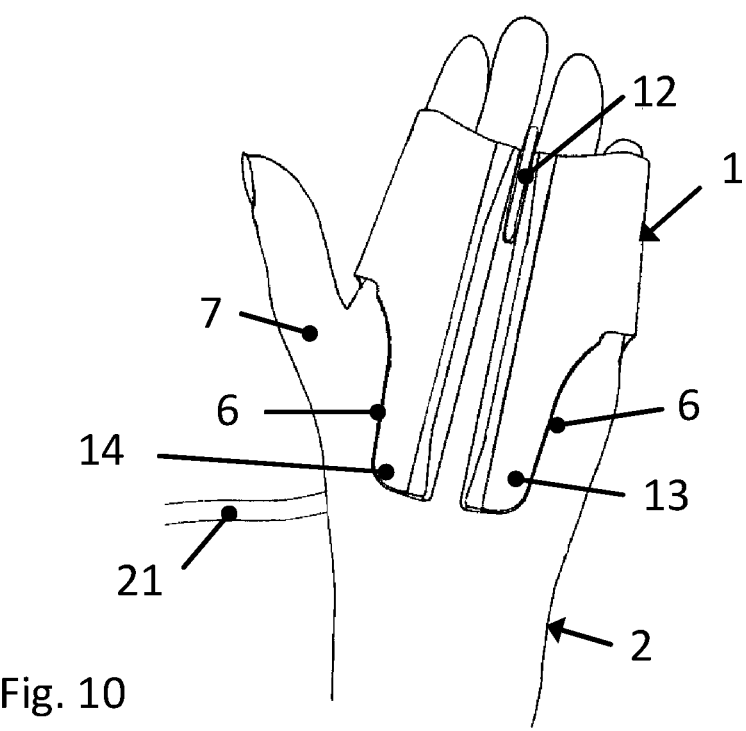

In FIG. 10, a view of the palmar section 5 of the handcuff 1 of FIG. 2 is shown, in which the left hand 2 of a user is located.

Figure 11:
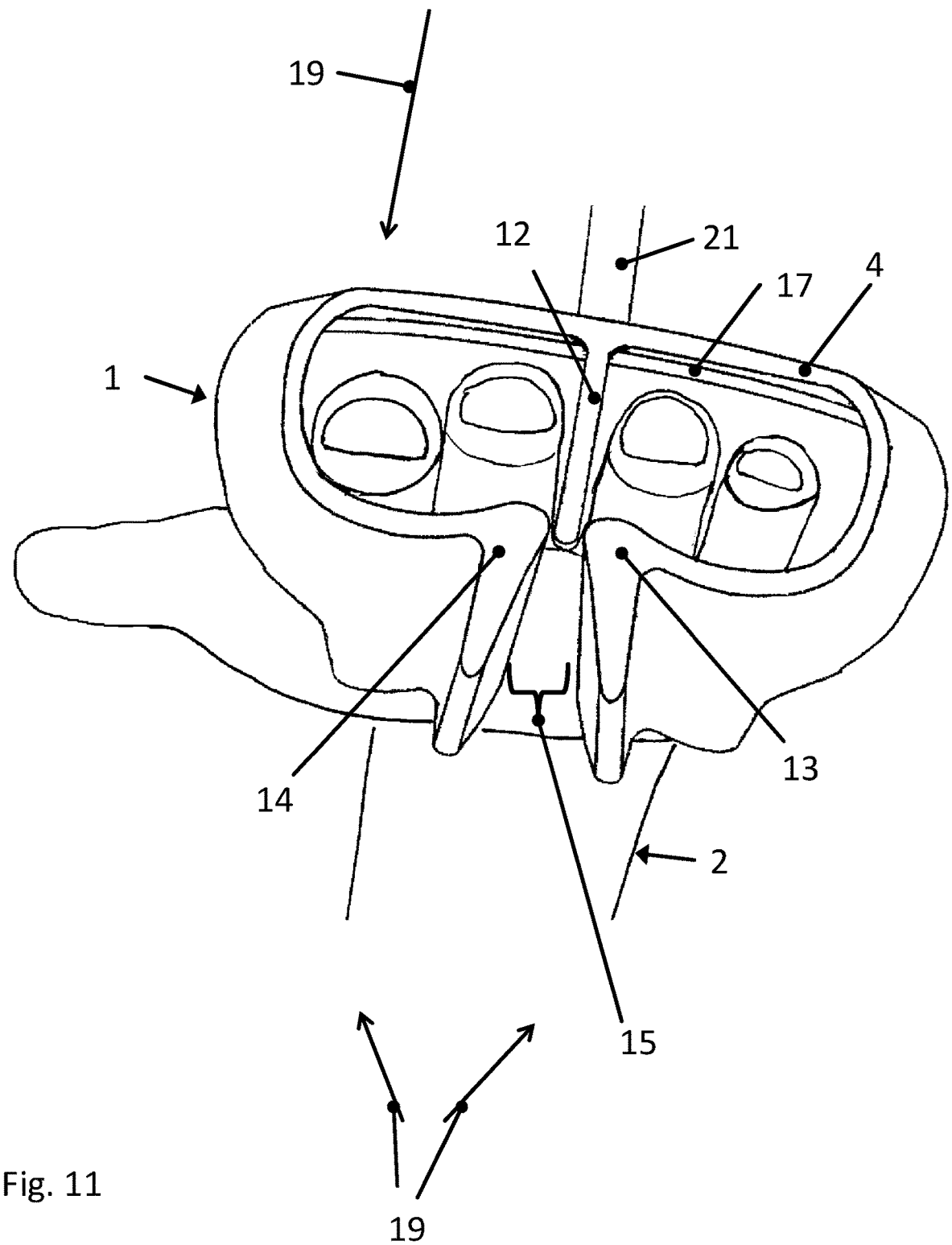

FIG. 11 shows a view of the distal end 9 of the handcuff 1 of FIG. 2, in which the left hand 2 of a user is located. In FIG. 11, the hand 2 and the handcuff 1 are shown at a moment during the insertion of the hand 2, before the hand 2 has fully entered the handcuff 1. The dorsal side of the hand 2 is not yet in contact with the pressure build-up element 17.

Figure 12A:
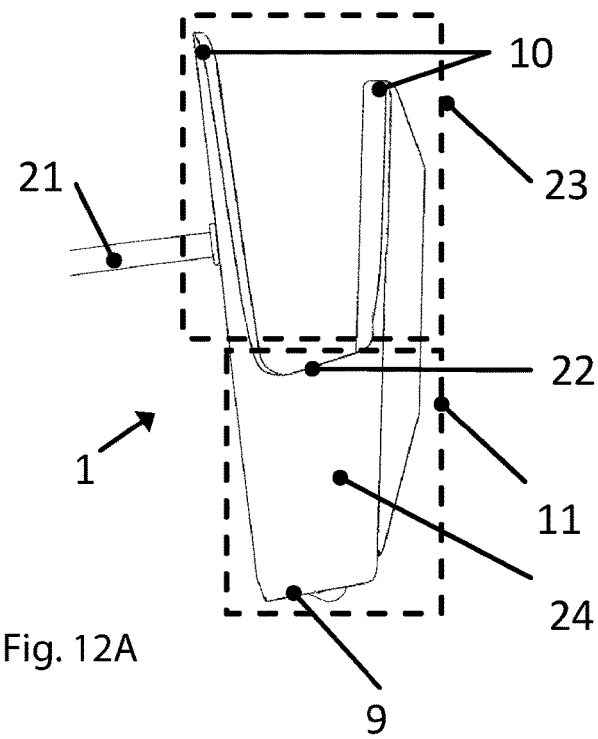
Figure 12B:
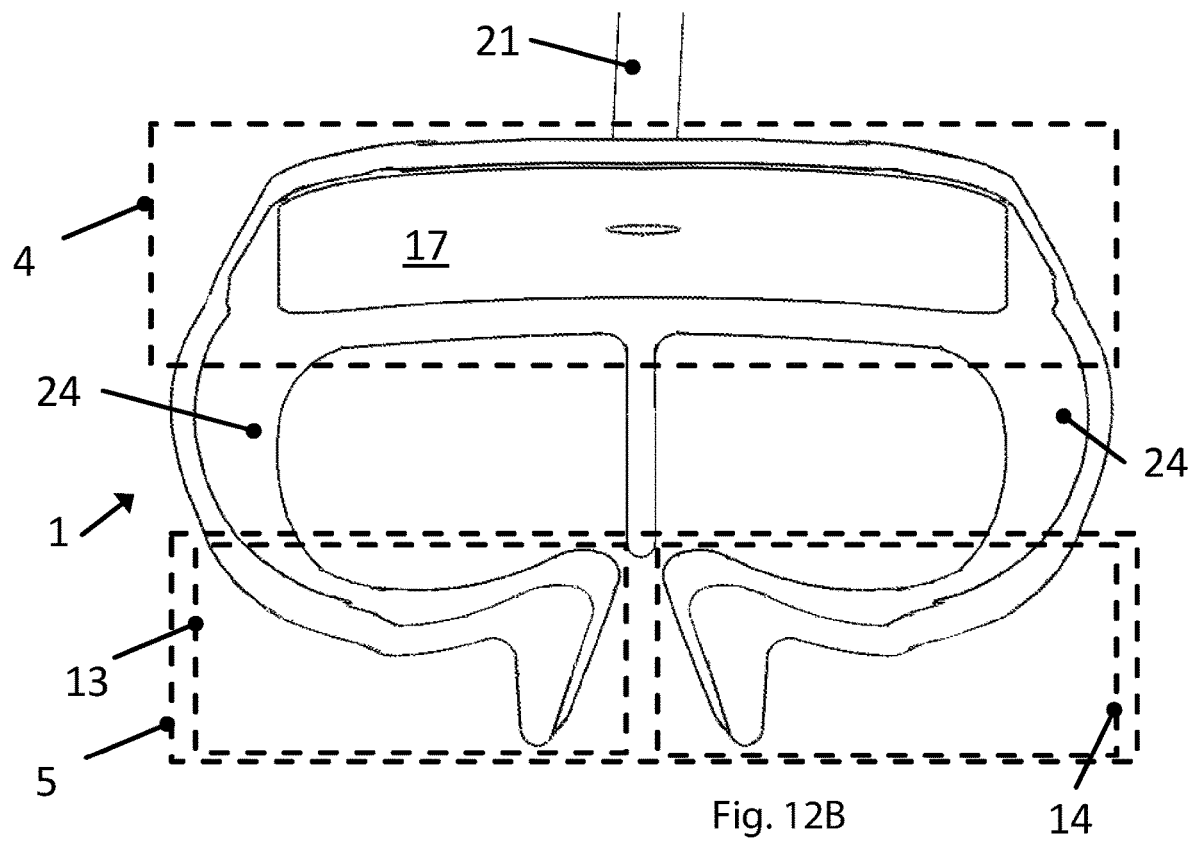

In FIGS. 12A and 12B, views of the handcuff according to FIGS. 4 and 5 are shown to illustrate the position and extent of the various sections 4, 5, 11, 24, 13, 14.

Figure 13:
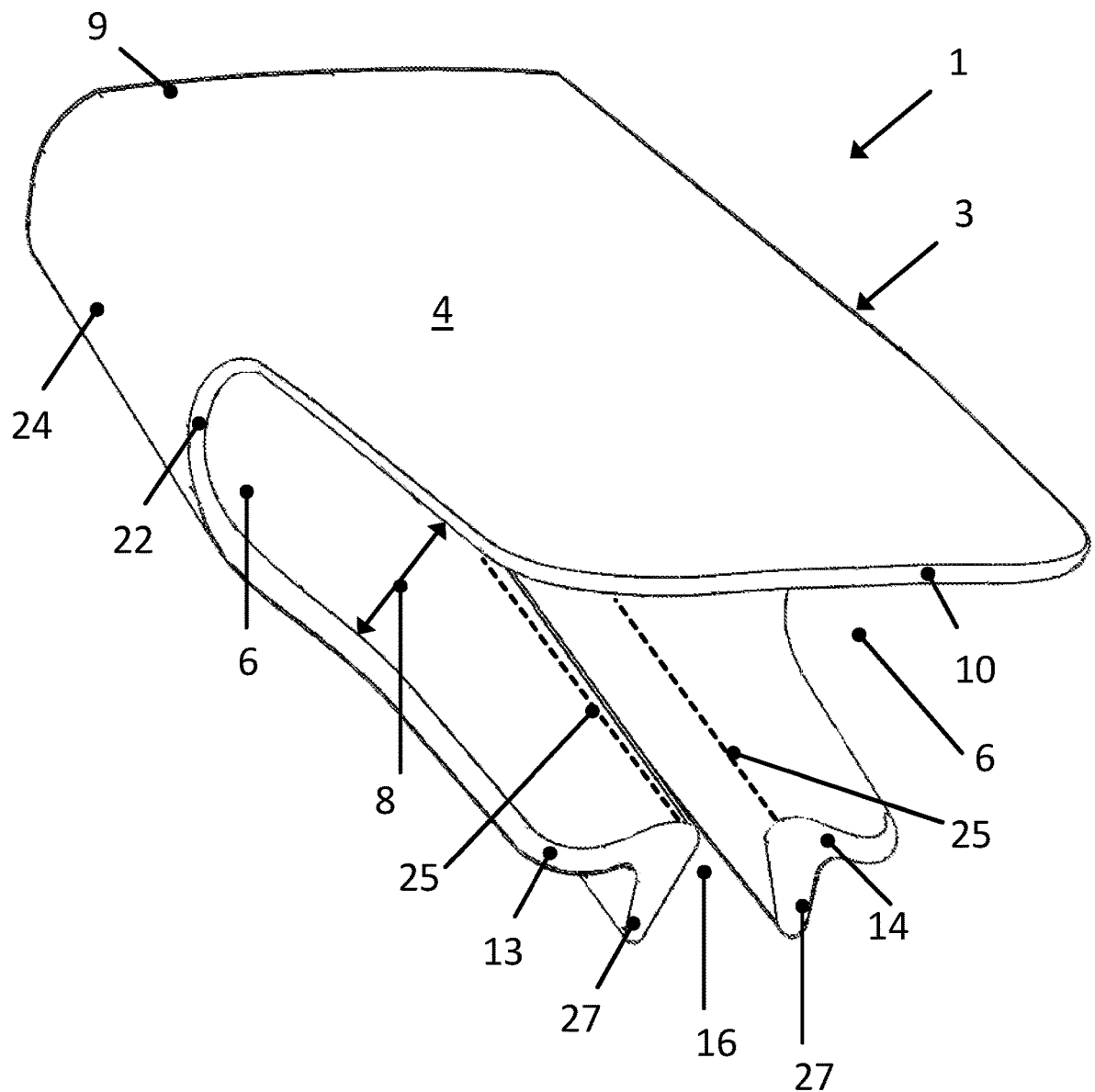
FIG. 13 shows a third, simple embodiment of a handcuff.

The handcuff 1 according to FIG. 13 does not require an air cushion and consists exclusively of the base body 3.

Figure 14A:
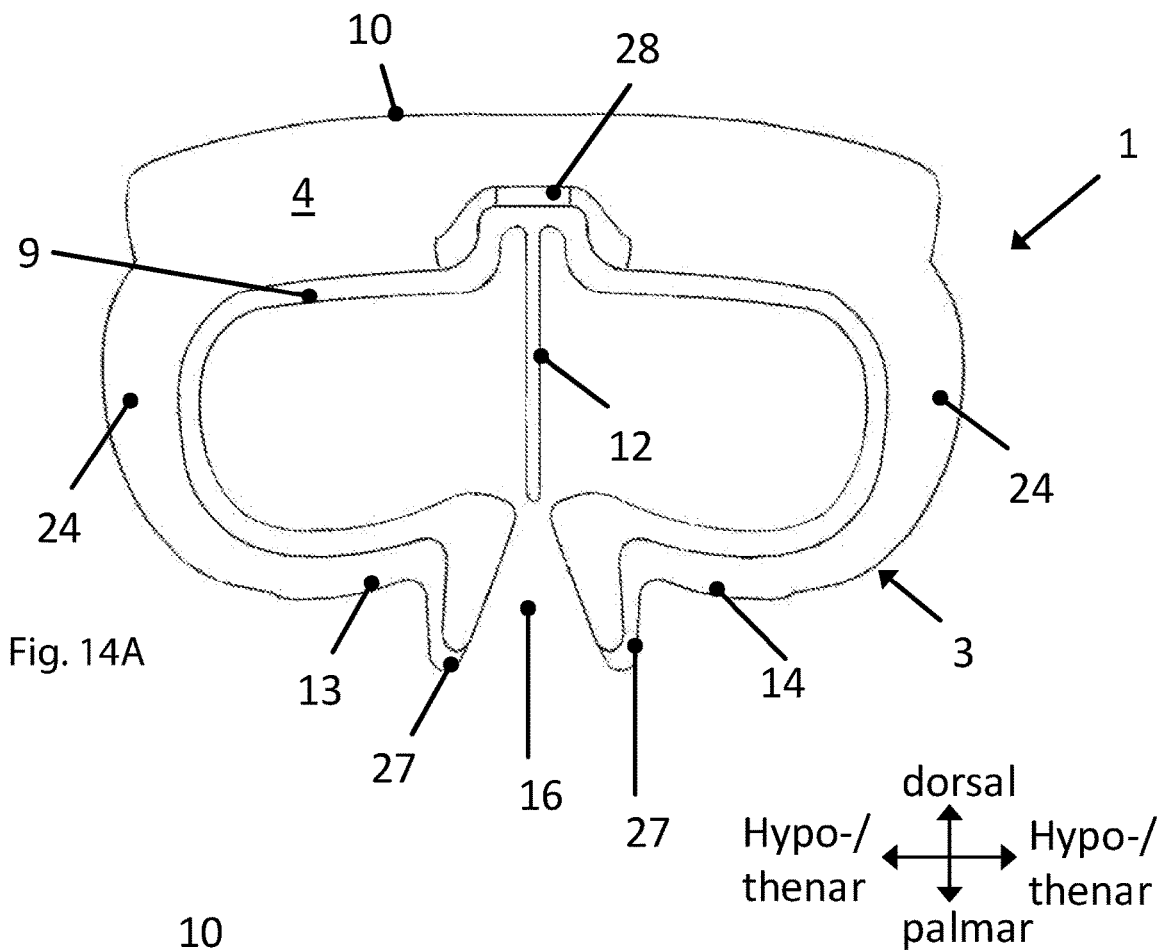
FIGS. 14A and 14B show a fourth embodiment of a handcuff.
Figure 14B:
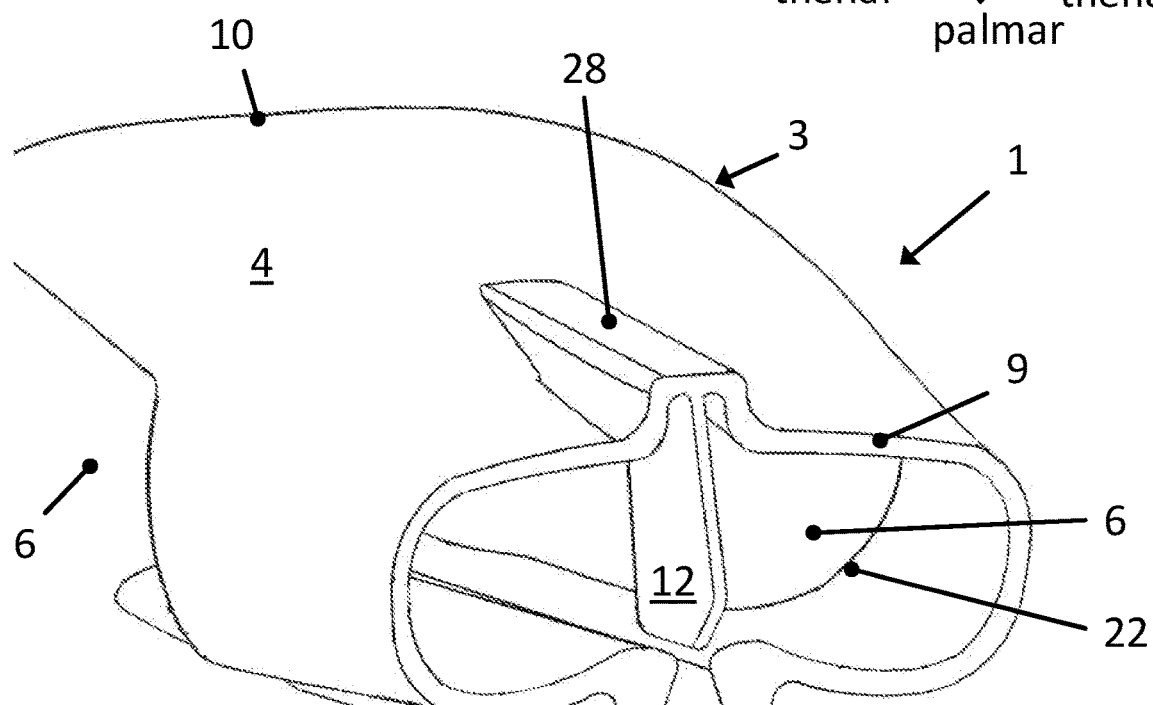

The handcuff 1 according to FIGS. 14A and 14B comprises a flexible guiding ridge 12. In order to better illustrate this, FIG. 14B shows a section of a handcuff 1 according to FIG. 14A from a slightly different perspective.

Figure 15:
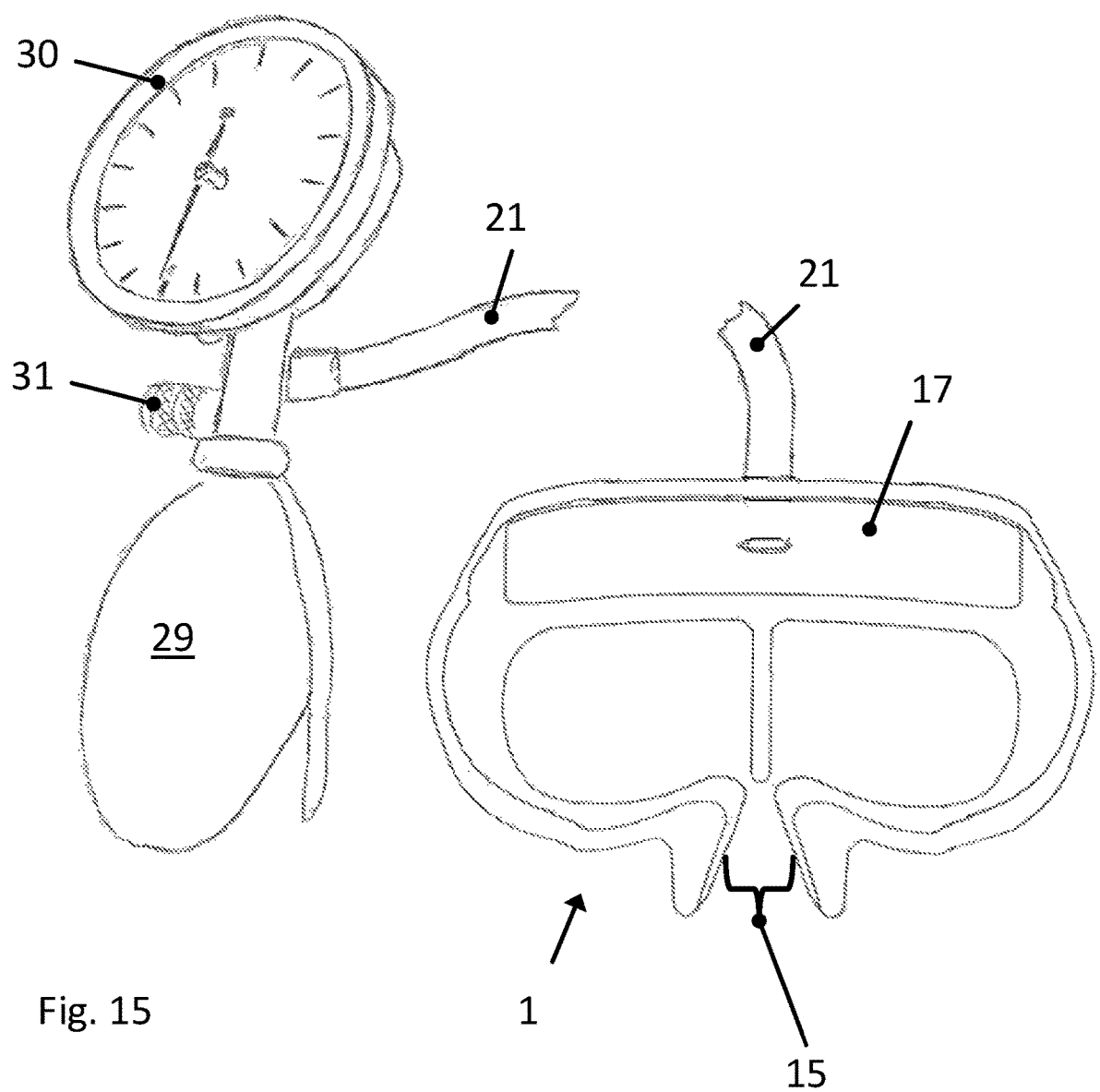
FIG. 15 shows the second embodiment of a handcuff according to FIG. 5 with a pump ball 29.

FIG. 15 shows the handcuff 1 according to FIG. 5, whereby most of the reference figures have been omitted for the purpose of clarity. FIG. 15 illustrates how this handcuff 1 is connected via the hose 21 to a pump ball 29, which in turn is equipped with or connected to a manometer 30 and a hand-operated valve 31. The hose 21, which connects the pump ball 29 and the handcuff 1, is not shown in its entirety for the purposes of clarity.

Figure 16:
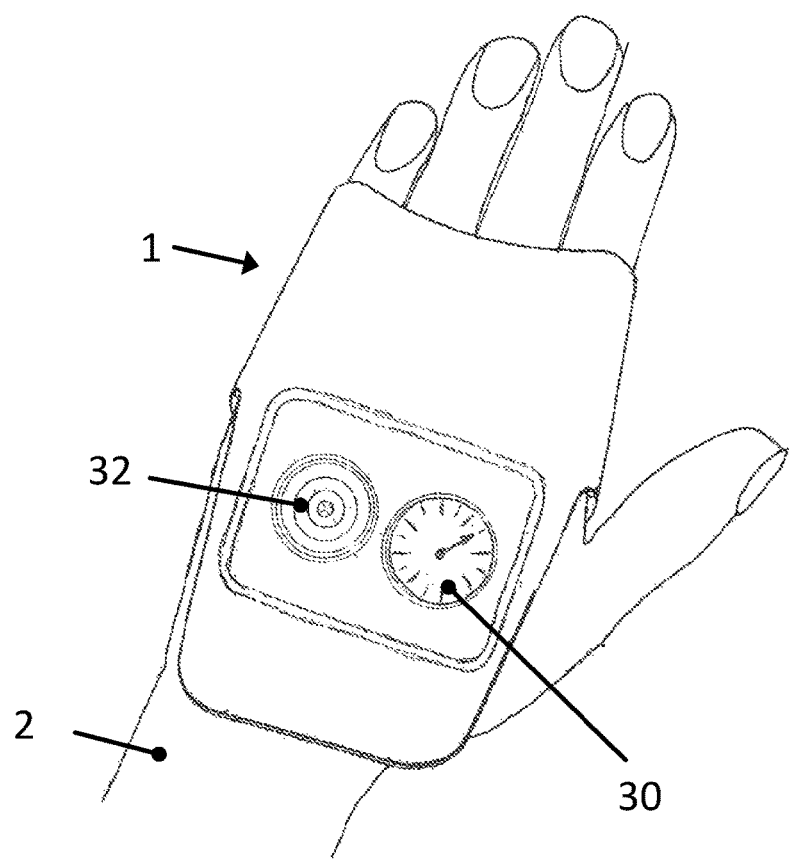
FIGS. 16 and 17 show a fifth embodiment of a handcuff with a built-in pump in the base body.
Figure 17:
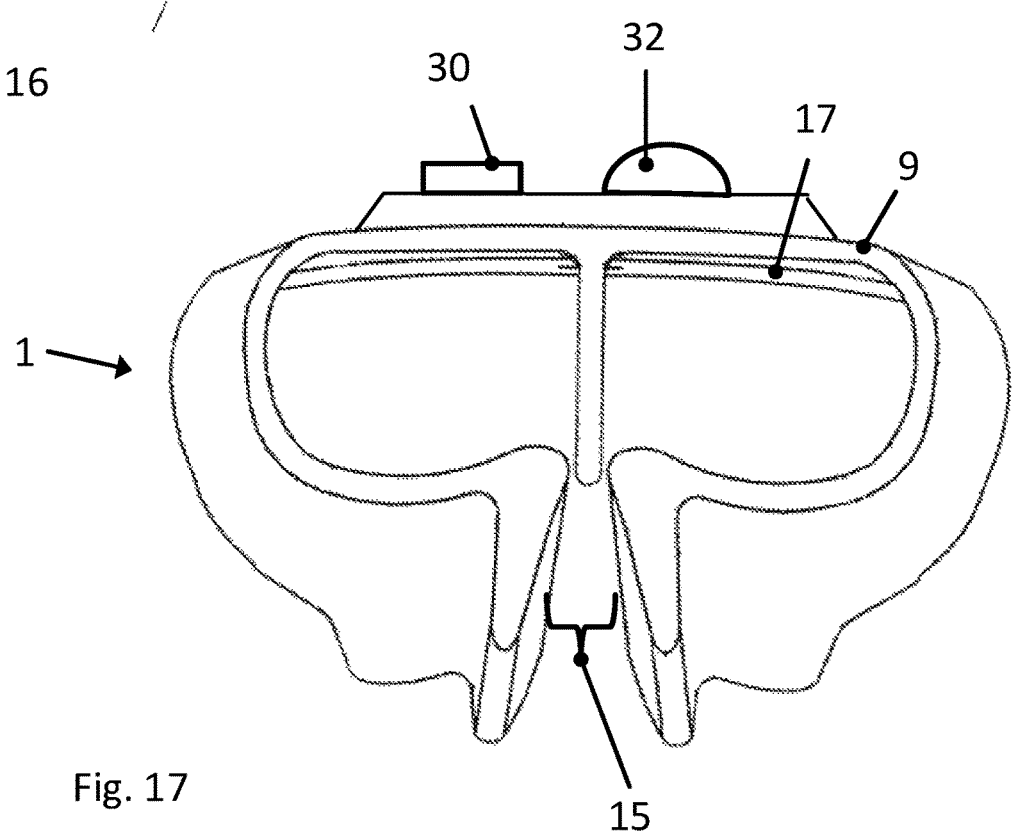

FIGS. 16 and 17 show an alternative embodiment of a handcuff 1, which has an built-in pump 32 and a likewise built-in manometer 30. The view of the handcuff 1 in FIG. 17 corresponds to that in FIG. 6. For the purpose of clarity, most of the reference numerals have been omitted.

FIG. 16 shows the handcuff 1 according to FIG. 17 in the ready-to-use state after a user has inserted the hand 2.

With reference to FIGS. 1 to 17, the operation of a device according to the invention is explained as follows:

The proximal end 10 of the handcuff 1 can receive either the left or the right hand 2 of a user without the need to laboriously thread the thumb 7 into a hole for this purpose. Instead, when the hand 2 is inserted into the handcuff 1, the thumb 7 is simply extended outwardly through one of the two slots 6.

The very simply embodiment shown in FIG. 1 is oval shaped in profile and does not include an opening 16. Furthermore, the width and distance between the dorsal and palmar sections 4, 5 along an imaginary distal-proximal axis are identical or invariable. When inserting the hand 2 (not shown), the carpal tunnel is placed between the two specially shaped sections 20, which are located on the palmar section 5. Since the proximal section of the hand 2 is higher in the dorsal-palmar direction than the distal section of the hand, the hand 2 is increasingly pressurized by the specially shaped sections 20 from both the dorsal and palmar sides during the insertion into the handcuff 1. This pressure causes a widening of the carpal tunnel in the manner known from generic handcuffs. The effective direction of the pressure exerted by the two specially shaped sections 20 on the palmar section 5 of the handcuff is indicated by arrows 19.

The handcuff 1 according to FIGS. 2 to 12 and 15 differs in some details from the very simply built handcuff 1 according to FIG. 1.

In the handcuff 1 shown in FIGS. 2 to 12 and 15, the hand 2 is also inserted into the proximal end 10 of the handcuff 1.

As shown in FIG. 4, the distance 8 between the dorsal section 4 and the palmar section 5 decreases towards the distal end 9. This in itself helps to build up the desired pressure on the palmar region of the hand 2 as the hand 2 is increasingly inserted into the handcuff 1.

Furthermore, when the hand 2 is inserted, the pressure exerted by the hand 2 on the base body 3 increases the distance 15 between the hypo/thenar sections 13, 14, which also in itself contributes to the desired pressure on the palmar region of the hand 2 for the purpose of widening the carpal tunnel.

In addition, the handcuff 1 according to FIGS. 2 to 12 and 15 comprises a pressure build-up element 17 in the form of an air cushion, which can be inflated via a compressor or by hand. For manual inflation, in particular a ball ("pump ball") known from blood pressure measuring devices can be used, as shown in FIG. 15. An alternative embodiment as shown in FIGS. 16 and 17 is also conceivable. In both cases, the air is introduced into the air cushion 17 via the hose 21. This again builds up pressure on the contact sections between the hand 2 and the handcuff 1, these contact sections being the air cushion 17 attached to the dorsal section 4 and the hypo/thenar sections 13, 14 forming the palmar section 5, and there preferably the contact lines 25 explained further below. When the air cushion 17 is inflated, the internal volume of the handcuff 1 is reduced, which ultimately results in pressure being exerted to the hand 2 from the dorsal and palmar directions. The pressure acting on the dorsal side or in the dorsal region of the hand 2 here essentially runs from dorsal to palmar.

The pressure acting on the palmar side or in the palmar region of the hand 2 is oblique. It thus comprises a component that acts in the dorsal palmar direction and a component that acts in the (hypo)thenar direction. This situation is indicated by the directions of action 19 in FIGS. 1 and 11, respectively above and below the dorsal and palmar sections 4, 5. Here, the desired effective direction in the case of the handcuff 1 shown in FIG. 1 is ensured by the orientation of the specially shaped sections 20. In the handcuff 1 shown in FIGS. 2 to 12 and 15 to 17, on the other hand, the direction of action is additionally and preferably mainly provided by the fact that the distance 15 increases during the pressure build-up. Since the two hypo/thenar sections 13, 14 or, in particular, the contact lines 25 have preferably already come into contact with the palmar region of the hand 2 during the pressure build-up, the carpal tunnel is effectively widened when the distance 15 increases. The same effect can be achieved in the embodiments according to FIGS. 13 and 14 during the insertion of the hand 2 into the base body 3.

The view according to FIG. 5 clearly shows that the air cushion 17, due to its flat shape, preferably exerts a flat pressure on the dorsal side of the hand 2. In contrast, the two imaginary contact lines 25 of the hypo/thenar sections 13, 14 exert a linear (as opposed to planar) pressure on the palmar side of the hand, due to their linear extension.

It is clearly visible in FIG. 5 that the hypo/thenar sections 13, 14 each comprise a convex section 26 in cross-section. This ensures that when the hand is inserted (shown from FIG. 7), the contact between the hand and the palmar section 5 takes place exclusively or at least primarily via the (imaginary) contact lines 25, and these introduce the desired pressure at the effective points for the treatment of carpal tunnel syndrome. The palmar section 5 is thus designed in such a way that only linear sections, indicated by the imaginary contact lines 25, effectively introduce pressure into the hand.

FIGS. 5 and 6 further show protrusion 27 near the contact lines 25, i.e., near the two ends of the hypo/thenar sections 13, 14 oriented towards the opening 16. These protrusions 27 increase the stability in the area of the (imaginary) contact lines 25, i.e. at the point of application of force into the hand to be treated.

In FIG. 12A, the distal section 11 and the proximal section 23 of the handcuff 1 are indicated by dashed boxes.

FIG. 12B shows the dorsal section 4 and the palmar section 5, whereby the latter is divided into the two hypo/thenar sections 13, 14.

The very simply built embodiment of a handcuff 1 according to the invention, shown in FIG. 13, consists of either a flexible or a rigid material. In either case, the distance 8 between the dorsal section 4 and the palmar section 5 and, if necessary, the flexible material is chosen so that the hand is slightly squeezed during the insertion. The pressure thus generated, which is transmitted to the palmar side of the hand via the hypo/thenar sections 13, 14 and in particular via the imaginary contact lines 25 respectively, causes the desired widening of the carpal tunnel in the manner already described.

If the handcuff 1 shown in FIG. 13 is made of a flexible material, the distance 8 between the dorsal section 4 and the palmar section 5 is increased when the hand is inserted, which in turn generates a restoring force with which the hypo/thenar sections 13, 14 exert the aforementioned pressure on the contact lines 25 in the effective direction 19 on the hand 2.

The following applies to handcuffs 1 with pressure build-up element 17 according to FIGS. 2 to 12 and 15 to 17: After inserting the hand 2 into the handcuff 1, the dorsal section 4 already exerts pressure on the dorsal side of the hand—depending on the size of the hand—even without inflating the pressure build-up element 17. This pressure is shown in FIG. 11 by a single arrow 19 above the dorsal section 4. Furthermore, also depending on the size of the hand, the two hypo/thenar sections 13, 14, especially at the contact lines 25, already exert a certain pressure on the palmar side of the hand. Initially, this pressure does not necessarily have to be oblique, i.e. in the direction of the two arrows 19 below the handcuff 1 in FIG. 11, but can also run in the opposite direction to the arrow 19 above the handcuff 1 in FIG. 11 and parallel to this arrow 19 (so "upwards", so to speak).

If the pressure build-up element 17 is increased (i.e. the air cushion is inflated), the pressure exerted on the hand by the dorsal section 4 in the direction of the arrow 19 shown above the handcuff 1 in FIG. 11 increases. With increasing inflation of the pressure build-up element 17, the two hypo/thenar sections 13, 14 preferably lie so close to the palmar side of the hand 2 that the distance 15 increases with even further inflation of the pressure build-up element 17. As a result, the effective directions 19 of the hypo/thenar sections 13, 14 indicated below the handcuff 1 in FIG. 11 are established, which act on the palmar side of the hand at the contact lines 25. Since they act on both sides of the carpal tunnel, the latter is widened as desired.

It should be noted with reference to all embodiments of the handcuff 1 that the guiding ridge 12 does not necessarily have to protrude beyond the distal end 9. This protrusion means that the length of the base body 3 can be kept short, but the fingers are still effectively guided by the extended guiding ridge 12. However, the guiding ridge 12 could also be shorter than shown in the figures; even a short guiding ridge 12 can guide the fingers sufficiently effectively. In particular, it is also conceivable that it is located completely inside the handcuff 1. Furthermore, in all embodiments, the guiding ridge 12 can also be dispensed with.

The fourth embodiment of a handcuff 1 is shown in FIGS. 14A and 14B in various perspectives. It differs from the handcuff 1 according to FIG. 13 in that the guiding ridge 12 is designed to be flexible. The guiding ridge 12 according to FIGS. 14A and 14B can curve in the hypo/thenar direction, i.e., so to say to the left or to the right. The hypo/thenar direction and the dorsal and palmar directions are indicated by arrows with regard to FIGS. 14A and 14B.

The advantage of a flexible guiding ridge 12 is that although the handcuff 1 is symmetrical in design and can receive both hands of a user, the left and right hands are usually not completely symmetrical. The common width of the middle finger and index finger is usually slightly larger than the common width of the ring finger and little finger. This can result in the middle finger and index finger being somewhat squeezed between the guiding ridge 12 and the side part 24, while the ring finger and little finger lie very loosely between the guiding ridge 12 and the opposite side part 24. The flexible guiding ridge 12 allows the middle finger to push the guiding ridge 12 a bit in the hypo/thenar direction toward the ring finger, giving the middle and index fingers more room.

The flexibility can be ensured on the one hand by the width or thickness of the guiding ridge 12. The thinner the guiding ridge 12, the easier it is to bend or flex it. In addition or alternatively, the bulge 28 shown in FIGS. 14A and 14B can be provided, which increases a length (measured along the dorsal-palmar axis) of the guiding ridge 12 with an otherwise unchanged height of the base body 3, because the lever on which the middle finger engages becomes larger than in the handcuff 1 according to FIG. 13.

Alternative designs are conceivable for making the guiding ridge 12 flexible or movable in the hypo/thenar direction. This can be done via material selection, dimensions, installation of joints, etc.

The embodiment comprising a flexible guiding ridge 12 with a bulge 28 according to FIGS. 14.1 and 14.2 is optional and can be used both in connection with handcuffs 1 without air cushion 17 (according to FIGS. 1 and 13) and in connection with handcuffs 1 with air cushion 17 (according to FIGS. 2 to 12 and 15 to 17).

A comparison of FIGS. 1 and 5 shows that a linear pressure introduction into the hand can be accomplished in different ways. In the embodiment according to FIG. 1, the specially shaped sections 20 effect the linear pressure introduction, which is indicated by the (imaginary) contact lines 25 in FIG. 1. In the embodiment according to FIGS. 2 to 17, on the other hand, the linear pressure introduction is effected by the shaping of the hypo/thenar sections 13, 14, in particular by their convex sections 26. This shaping has the effect that the contact between palmar section 5 and hand is effected primarily or exclusively via the contact lines 25.

Of course, other possibilities are conceivable to ensure a linear pressure introduction. In particular, alternatively shaped specially shaped sections 20, an alternative shaping or a combination of both are conceivable.

The increased stability, which in the embodiment examples according to FIGS. 2 to 17 is effected by the protrusions 27, can of course also be produced in other ways. For example, increased rigidity of the material, possibly only in the region near the opening 16, may be considered. Further, inlays of metal or other material imparting stability, ribs or the like may also be thought of. Furthermore, there may be embodiments in which the intrinsic stability of the base body is sufficient and no measures to increase stability are necessary.

Starting from the situation shown in FIG. 16, the user can pump up the pressure build-up element 17 by actuating the integrated pump 32, which functions analogously to the pump ball 29, while controlling the pressure with the aid of the manometer 30. For this purpose, the built-in pump 32 is fluidically connected to the pressure build-up element 17, as is also the case for the pump ball 29 and the pressure build-up element 17 in the embodiment according to FIG. 15. A valve with which the pressure can be released from the pressure build-up element 17 after completion of the treatment is provided, but cannot be seen in FIGS. 16 and 17.

The invention claimed is:

1. A handcuff for treatment of carpal tunnel syndrome of a hand, the handcuff comprising:
a base body including a dorsal section and a palmar section;
wherein the palmar section comprises two hypo/thenar sections, and the two hypo/thenar sections are separated by an opening;
wherein the base body includes a distal section with two side parts that connect the two hypo/thenar sections and the dorsal section;
wherein the dorsal section is adapted to exert a pressure on a dorsal side of the hand on at least one location;
wherein the palmar section is arranged to exert a pressure on a palmar side of the hand on both sides of a carpal tunnel respectively on at least one location;
wherein the dorsal section and the palmar section are adapted to widen the carpal tunnel of the hand by exertion of the pressure;
wherein the base body has two substantially opposite open slots between the dorsal section and the palmar section;
wherein distal slot ends of the open slots are directly adjacent to the two side parts;
wherein the open slots are disposed in a proximal end and are adapted to receive a thumb of a left or a right hand, the distal section configured to receive remaining fingers of the hand.

2. The handcuff according to claim 1, wherein a distance between the dorsal section and the palmar section increases from a distal end towards a proximal end of the base body.

3. The handcuff according to claim 1, including at least one guiding ridge in a distal section of the base body, wherein the at least one guiding ridge is arranged between pairs of two fingers of the hand in a position of use, thus ensuring an orientation of the hand effective for treatment.

4. The handcuff according to claim 1, wherein the base body is resiliently arranged in such a way that, when inserting the hand, a distance between the dorsal section and the palmar section increases, as a result of which the pressure for widening the carpal tunnel is provided in a position of use.

5. The handcuff according to claim 1, wherein a distance between the first hypo/thenar section and the second hypo/thenar section can vary.

6. The handcuff according to claim 1, including a pressure build-up element that contacts the dorsal section, wherein the pressure build-up element is arranged to exert pressure on the dorsal side of the hand on at least one location.

7. The handcuff according to claim 1, wherein the base body is a one-piece base body.

8. The handcuff according to claim 1, wherein the base body has a C-shape in profile.

9. The handcuff according to claim 1, wherein the base body is made of plastic.

10. The handcuff according to claim 1, wherein the base body is made of an elastic material.

11. The handcuff according to claim 1, wherein a width, which is measured in a thenar-hypothenar direction, increases from a distal end to a proximal end of the base body.

12. The handcuff according to claim 1, wherein the opening defines a distance between the two hypo/thenar sections.

13. The handcuff according to claim 12, wherein the distance increases during a pressure buildup.

14. A method, comprising:
providing a handcuff for treatment of carpal tunnel syndrome of a hand, the handcuff including a base body with a dorsal section, a palmar section with two hypo/thenar sections separated by an opening, and two open slots with an elongated shape disposed between the dorsal section and the palmar section, wherein the two open slots are disposed in a proximal end and are adapted to receive a thumb of a left or right hand;
arranging the dorsal section to exert a pressure on a dorsal side of a hand;
arranging the palmar section to exert a pressure on a palmer side of a hand; and
opening one of the two open slots to receive a thumb of a left hand or a right hand.

15. The method according to claim 14, including increasing a distance between the dorsal section and the palmar section from a distal end towards a proximal end of the base body.

16. The method according to claim 14, including:
providing at least one guiding ridge in a distal section of the base body;
arranging the at least one guiding ridge between two fingers of the hand in a position of use; and
establishing an orientation of the hand for treatment.

17. The method according to claim 14, including:
providing a pressure build-up element on the dorsal section; and
arranging the pressure build-up element to exert pressure on the dorsal side of the hand.

18. The method according to claim 14, including forming the base body as one unitary piece.

19. The method according to claim 14, including providing a profile of the base body with a C-shape.

20. The method according to claim 14, including comprising the base body of plastic or an elastic material.

21. The method according to claim 14, including increasing a width of the base body from a distal end to a proximal end of the base body.

* * * * *